US00PP16474P3

(12) United States Plant Patent
Khanuja et al.

(10) Patent No.: US PP16,474 P3
(45) Date of Patent: Apr. 25, 2006

(54) MINT PLANT NAMED 'CIM INDUS'

(50) Latin Name: *Mentha piperita*
Varietal Denomination: Cim Indus

(75) Inventors: Suman Preet Singh Khanuja, Lucknow (IN); Nirmal Kumar Patra, Lucknow (IN); Ajit Kumar Shasany, Lucknow (IN); Birendra Kumar, Lucknow (IN); Soni Gupta, Lucknow (IN); Rakesh Kumar Upadhyay, Lucknow (IN); Togarrati Padma Priya, Lucknow (IN); Anil Kumar Singh, Lucknow (IN); Mahendra Pandurang Darokar, Lucknow (IN); Virendra Kumar Singh Tomar, Lucknow (IN); Janak Raj Bahal, Lucknow (IN); Raj Kishori Lal, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 92 days.

(21) Appl. No.: 10/749,906

(22) Filed: Dec. 29, 2003

(65) Prior Publication Data

US 2005/0150027 P1 Jul. 7, 2005

(51) Int. Cl.
*A01H 5/00* (2006.01)

(52) U.S. Cl. ..... Plt./259
(58) Field of Classification Search ..... Plt./259
See application file for complete search history.

*Primary Examiner*—Anne Marie Grunberg
*Assistant Examiner*—June Hwu
(74) *Attorney, Agent, or Firm*—Merchant & Gould P.C.

(57) ABSTRACT

The present invention relates to a new and distinct mint plant of *Mentha piperita* 'Cim Indus', selected through screening, field trial and analysis of monoterpene constituents of the essential oil of the germplasm, possessing the characters of producing high amount of menthofuran ranging between 22 to 30% of total oil content, high amount pulegone ranging between 9.0 to 18% of total oil content, with essential oil content ranging between 0.32 to 0.40% of the total oil content.

3 Drawing Sheets

FIELD OF THE INVENTION

Genus, Species, and Variety

The present invention relates to a new and distinct mint plant of the genus *Mentha,* species *piperita,* designated the variety 'Cim Indus'.

This variety was selected through screening, field trial and analysis of monoterpene constituents of the essential oil of the germplasm. This variety possesses the characters of producing high amount of menthofuran ranging between 22 to 30% of total oil content, high amount pulegone ranging between 9.0 to 18% of total oil content, with essential oil content ranging between 0.32 to 0.40% of the total oil content.

BACKGROUND OF THE INVENTION

Menthofuran (3,6-dimethyl-4,5,6,7-tetrahydrocoumarone) is one of the major constituent for aroma of the essential oil extracted from the leaves of *Mentha piperita.* Because any other compound has not duplicated the aroma effect, menthofuran is important in the formulation of certain standardized essential oils, such as peppermint oil. However, menthofuran is an expensive compound of limited availability as the plants produce 0 to 6% menthofuran (U.S. Plant Pat. No. PP11,788). Literatures are available for the chemical synthesis of menthofuran to substitute the naturally available menthofuran (U.S. Pat. No. 4,240,969) to reduce cost of production. Also the acceptability of synthetic menthofuran is a limiting factor in determining the cost of the essential oil mixture containing synthetic components in aroma industry.

Considering the importance of menthofuran in aroma industry under 'New Millennium Indian Technology Initiative (NMITLI) programme' launched by Council of Scientific and Industrial Research (CSIR), India, during 2001, a systematic approach was undertaken to evaluate the existing germplasm of *M. piperita* at CIMAP and breed for genetic enhancement towards high menthofuran biosynthesis in the essential oil. Systematic breeding experiments to allow open pollination followed by single seed progeny selection by chemotypic evaluation for enhanced constituent (menthofuran) led to development of this chemotype the variety 'Cim Indus'.

OBJECTS OF THE INVENTION

The main object of the present invention is to develop a new and distinct mint plant.

Another main object of the present invention is to develop a novel mint plant through screening, field trial and analysis of monoterpene constituents of the essential oil of the germplasm.

Yet another object of the present invention is to develop a plant producing high amount of menthofuran.

Still another object of the present invention is to develop a plant producing high amount pulegone.

Still another object of the present invention is to develop a plant producing high herbage.

Still another object of the present invention is to develop a mint plant showing resistance against major plant disease conditions like leaf spot, rust, powdery mildew, lepidopteran pest *Spilarctia obliqua.*

SUMMARY OF THE INVENTION

The present invention relates to a new and distinct mint plant of *Mentha piperita* 'Cim Indus', selected through screening, field trial and analysis of monoterpene constituents of the essential oil of the germplasm, possessing the characters of producing high amount of menthofuran ranging between 22 to 30% of total oil content, high amount pulegone ranging between 9.0 to 18% of total oil content, with essential oil content ranging between 0.32 to 0.40% of the total oil content.

DETAILED DESCRIPTION OF THE INVENTION

Figure 1:
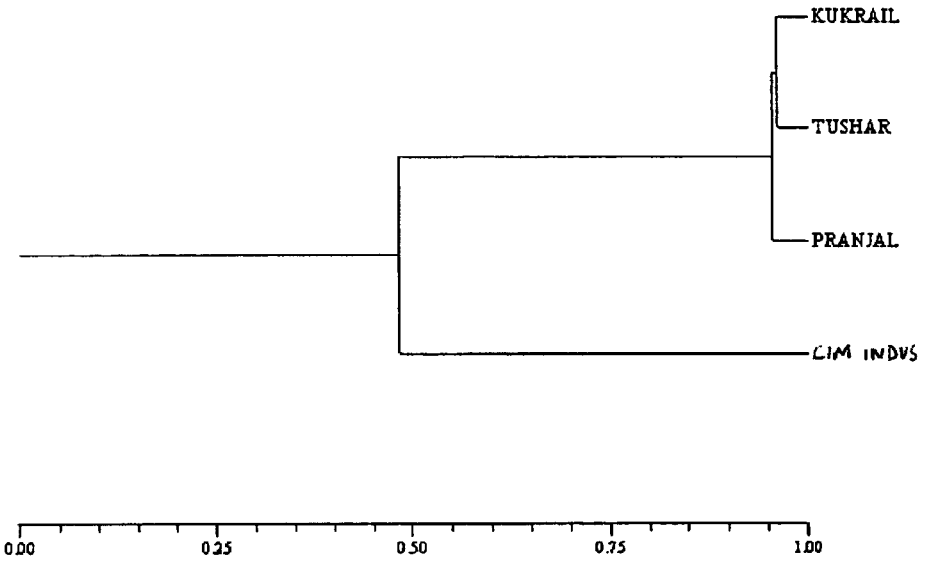
FIG. 1 shows cluster analysis for the chemotype "Cim Indus" compared to 'Kukrail', 'Tushar', and 'Pranjal'.

Accordingly, the present invention relates to a new and distinct mint plant of *Mentha piperita* 'Cim Indus', selected through screening, field trial and analysis of monoterpene constituents of the essential oil of the germplasm, possessing the characters of producing high amount of menthofuran ranging between 22 to 30% of total oil content, high amount pulegone ranging between 9.0 to 18% of total oil content, with essential oil content ranging between 0.32 to 0.40% of the total oil content.

The plant was developed at the CIMAP research farm, Lucknow, India and asexually propagated through suckers for further planting in the same farm. By appearance, this new variety is a typical plant of *Mentha piperita*. The difference between this new variety and the parent or other known varieties is in the herbage at menthofucan, pulegone and other essential components. Thus, this is a new and distinct mint plant of *Mentha piperita* variety 'Cim Indus', selected through screening, field trial and analysis of monoterpene constituents of the essential oil of the germplasm, possessing the following combination of characters:

a. the said plant produces high amount of menthofuran ranging between 22 to 30% of total oil content, b. the said plant produces high amount pulegone ranging between 9.0 to 18% of total oil content, c. the said plant produces essential oil content ranging between 0.32 to 0.40% of the total oil content, d. the said plant produces herbage yield ranging between 200–220 quintal per hectare, e. the said plant is of height ranging between 65 to 70 cms, with plant canopy of area ranging between 78–85 cms, f. the said plant shows resistance against leaf spot, rust, powdery mildew, lepidopteran pest *Spilarctia obliqua,* g. the said plant has Quadrangular, woody stems, of color purplish green with R.H.S. color code of 59A, the surface texture of the stem is hairy and rough, h. the said plant has simple, opposite, and decussate leaves, of with an upper surface of dark green color with color code of RHS 137A, and a lower surface of green color with color code of RHS 137C; the surface of the leaf is rough and hairy with purple violet colour (81 A) on lower veins;

i. the said plant has leaves of chartaceous texture, j. the said plant's leaves has Glabrous dorsal surface, with hairy on ventral veins, k. the said plant has leaves of ovate-elliptical shape, with serrate margins, l. the said plant has leaves with acute-acuminate tip, obtuse base, and broad size, m. the said plant has leaf with petiole of length ranging between 0.5 to 0.9 cm, n. the said plant has leaf with of area about 7.91 $cm^2$, o. the said plant has leaf with length ranging between 1.2 to 4.3 cm, p. the said plant has leaf width ranging between 0.6 to 2.6 cms, q. the said plant has inflorescence of nature terminal spike, r. the said plant has flowers of following traits:
   i. arranged in whorls,
   ii. smooth pedicel,
   iii. green color pedicel with R.H.S. code 137B,
   iv. calyx is glabrous, tubular, 5-lobed, margin ciliated, yellow green with R.H.S. color code of 146C,
   v. corolla is tubular, 4-lobed, with subsequeal lobes, and is light purple tending towards white, whitish purple: 76 D;
   vi. flowers are whitish purple: 76 D,
   vii. anthers are four in number, exserted, grayed-red with R.H.S. code of 181A,
   viii. stigma is bifid.

s. the said plant is able to produce higher herbage, menthofuran and pulegone yield per unit area as compared to other existing improved varieties, t. the said plant produce high menthofuran when harvested 75 days after planting and 115 days after planting.

u. the said plant produce high pulegone when harvested 75 days after planting, v. the said plant is able to produce higher pulegone and menthofuran due to up regulation and thus has the potential to isolate regulatory factors for monoterpene metabolism, and w. the said plant has distinct molecular profile by random amplified polymorphic DNA (RAPD) using 20 random primers (OPA) distinguishing the plant from the other existing varieties.

The flowers are arranged in whorls and the inflorescence grow which vary in length. The flowers include:

*Pedicel.*—1.0 to 1.5 mm in length, Yellow green (145C).

*Calyx.*—Four sepals, persistent, 1.0 to 2.5 mm in length, Yellow green (145B).

*Calyx diameter.*—1 mm.

*Calyx texture.*—Rough.

*Corrolla.*—Whitish purple (76D) 2.0 to 4.0 mm in length, composed of 4 petals, differentiated into tube and a limb.

*Corolla texture.*—Smooth.

*Androecium.*—Anthers — Four, ocidimetary, white, remain inside the corolla tube.

*Gynoecium.*—Stigma. Bifid, bicarpellary syncarpous; Ovary superior, deeply four-lobed, bilocular; Style gynobasic arising between the lobes of the ovary. Stigma — Red-Purple Group 71C. Color of ovaries — Yellow-Green Group 151A.

The leaves have predominantly the carvone and menthofuran smell. This variety produces no fruit and no seeds.

The present invention is related to the development of a novel high menthofuran and pulegone producing chemotype which can also yield high amount of pulegone through proper harvest management. The plant chemotype was obtained through screening of the open pollinated seed progenies of the variety 'Kukrail'. The invention is further related to the plant producing more herb yield leading to higher production of essential oil per unit area compared to the seed parent variety. The selected plant possesses the property of accumulating more menthofuran and pulegone at specific developmental stages and hence proper management prior to processing can yield high amount of these important phytochemicals for industrial use. This plant is unique and clearly distinct from all other existing varieties of *Mentha piperita*. The new plant type 'Cim Indus' can be propagated vegetatively through suckers and runners for commercial cultivation.

'Kukrail' is a released variety of CIMAP which is maintained along with the germplasm of CIMAP in the field systemically every year. Every year in the month of October, the twigs are planted in small sized plots (3 m×3 m) for generation of enough planting material for planting in the main field during the month of January. Open pollinated seeds are collected from different genotypes every year and analyzed for monoterpene constituents in the essential oil. 'Cim Indus' also known as CIMAP/MP20 is such a genotype selected from open pollinated seed progenies of the variety 'Kukrail'. *Mentha piperita* is propagated vegetatively through runners. With the NMITLI initiative the runners generated from the seed plots were planted in 5 m×5 m plots during the month of January 2001, following normal agronomic practices with the objective to screen genotypes rich in menthofuran in the essential oil. Replicated samples from each genotypes were taken from the field by planting multiplied runners in the month of January 2001, 2002 and 2003 for 3 consecutive years in RBD fashion and different growth and yield characteristics were recorded (Table 1). For yield trials the replicated plots were prepared by adding only FYM 1.5 ton per ha. The three-year averages of herb yield, essential oil yield and the variations in major essential oil components are detailed below for the genotype (CIMAP/MP20 compared to the CIMAP released varieties of *Mentha piperita* 'Kukrail', 'Tushar', 'Pranjal'. 'Pranjal' bears the U.S. Pat. No. 14,090.

TABLE 1

Comparative herbage, oil, menthofuran and pulegone yield of *Mentha piperita* genotypes.

| Genotypes | CIMAP/MP20 | Kukrail | Tushar | Pranjal |
|---|---|---|---|---|
| Oil content (%) | 0.35 | 0.40 | 0.63 | 0.55 |
| Herrbage yield (Quintal/hectare) | 206.8 | 123.8 | 190.5 | 123.8 |
| Oil yield (Litre per hectare) | 72.41 | 49.52 | 119.04 | 68.10 |
| Menthofuran content(%) | 27.24 | 8.727 | 9.648 | 8.385 |
| Calculated Menthofuran yield (Litre per hectare) | 19.72 | 4.32 | 11.484 | 5.710 |
| Pulegone(%) | 15.405 | 3.032 | 2.355 | 2.783 |
| Calculated Pulegone yield (Litre per hectare) | 11.155 | 1.501 | 2.80 | 1.89 |

If menthofuran is aimed the genotype can yield highest amount of natural menthofuran than any other variety released and reported which is the case for pulegone also.

Oil Extraction and GLC Analysis

Oil samples from the field grown plants were extracted by hydrodistillation using Clevenger's apparatus and weighed to record the yield. Over ground shoot samples were collected from the whole plant selected randomly from the middle of the row of each replicated plots at different days after planting (35. 55, 75, 95, 115 days after planting). Shoots collected from individual genotypes were bulked for each treatment plot and essential oil was distilled from all the replicates taking 500 g of bulked shoots containing leaves. The final analysis of all the essential oil samples was accomplished on Varian CX-3400 using a 30 m×0.25 mm Supelcowax-10 column. The injector and detector temperature were maintained at 200 and 225° C. respectively, with oven temperature programmed from 60 to 200° C. at the rate of 7° C. $min^{-1}$ increase, with initial and final holds of 2 and 5 minutes respectively. Hydrogen gas was used as carrier at the rate of 1 ml $min^{-1}$ and an aliquot of the sample was injected with a split ratio of 1:50. Data were processed in the electronic integrator Varian 4400 and the identification was based on retention time of authentic samples of 1-menthol (Takasago, Japan) and retention indices calculations (Jennings W & Shibamoto T (1980) Qualitative analysis of flavour and fragrance volatile by capillary GC, Academic Press Inc., New York.).

Table 2

Variation in major essential oil components of *Mentha piperita* genotype CIMAP/MP20 at different stages of growth.

| | 35 DAYS | 55 DAYS | 75 DAYS | 95 DAYS | 115 DAYS |
|---|---|---|---|---|---|
| Limonene | 0.6405 | 6.5948 | 5.6849 | 5.6283 | 4.484 |
| Menthone | 1.4922 | 48.55 | 2.0802 | 3.8298 | 1.9770 |
| Menthofuan | 1.4922 | 6.2713 | 23.96 | 3.4181 | 27.246 |
| Menthol | 32.5681 | 34.138 | 12.7920 | 28.2289 | 14.396 |
| Pulegone | 9.6714 | 0.2421 | 10.4367 | 16.8836 | 15.405 |

TABLE 3

Comparative monoterpene component profiles in the essential oil of *M. piperata* P(20), Kukrail, Tushar, Pranjal, 115 days after planting.

| | Components | CIMAP/MP20 | Kukrail | Tushar | Pranjal |
|---|---|---|---|---|---|
| 1 | α-Pinene | 0.432 | 0.465 | 0.661 | 0.707 |
| 2 | β-Pinene | 1.004 | 0.874 | 1.256 | 1.472 |
| 3 | Sabinene | 0.857 | 1.031 | 0.786 | 0.881 |
| 4 | Myrcene | 4.897 | 0.342 | 0.342 | 0.341 |
| 5 | α-terpinene | 0.081 | 0.244 | 0.089 | 0.069 |
| 6 | Limonene | 4.484 | 2.862 | 2.656 | 3.145 |
| 7 | 1,8 Cincole | 8.809 | 4.904 | 5.112 | 5.252 |
| 8 | γ-Terpinene | 0.769 | 0.226 | 0.244 | 0.248 |
| 9 | p-Cymene | 0.304 | 0.309 | 0.105 | 0.130 |
| 10 | 3-Octanol | 0.133 | 0.127 | 0.258 | 0.322 |
| 11 | Menthone | 1.970 | 21.292 | 28.248 | 28.339 |
| 12 | Menthofuran | 27.246 | 8.727 | 9.648 | 8.385 |
| 13 | Iso menthone | 0.556 | 3.963 | 4.410 | 4.084 |
| 14 | Menthyl acetate | 2.323 | 7.857 | 4.768 | 3.799 |
| 15 | Neo menthol | 4.757 | 3.870 | 2.897 | 3.288 |
| 16 | Caryophyllene | 0.661 | 0.452 | 0.088 | 0.056 |
| 17 | Pulegone | 15.405 | 3.032 | 2.355 | 2.783 |
| 18 | Menthol | 14.396 | 28.840 | 26.818 | 26.147 |
| 19 | Piperitone | 1.536 | 2.331 | 1.056 | 1.232 |
| 20 | Carvone | 0.606 | 0.376 | 0.585 | 0.796 |

The genotype CIMAP/MP20 has a characteristic oil profile which expresses differentially at different stages of growth. The menthofuran content was found to be higher at 75 days stage which decreased during 95 days and again increased during harvesting time 115 days. Corresponding menthol content in the essential oil content was found to be negatively correlated to the menthofuran content at corresponding stages of growth.

Pulegone content increased after 75 days and was stabilized after 95 to 115 days (Table 2). The comparative monoterpene profiles for different components is presented in Table 3 during harvesting time (115 days stage).

Trichome Analysis of the Genotype CIMAP/MP20

Monoterpenes are known to be cytotoxic to plant tissues, inhibiting respiration and photosynthesis by drastically affecting the mitochondria, golgi bodies etc and decreasing cell membrane permeability (Brown J T, Hegarty P K & Charlwood B V (1987) The toxicity of monoterpenes to plant cell cultures. Plant Science 48:195–201.). Monoterpenes are either sequestered in the plants in specialized structures like glandular hairs in *Pelargonium* (Brown J T & Charlwood B V (1986) Differentiation and monoterpene biosynthesis in plant cell cultures. In; Morris P, Scragg A, Stafford A and Fowler M (eds) Secondary Metabolism in Plant Cell Cultures. Cambridge University Press, Cambridge, 1986, p.68.), trichomes in *Mentha* or stored in the form of non-toxic glycoside derivatives in vacuoles e.g. *Rosa* spp.

So the number of trichomes at different developmental stages of the genotype CIMAP/MP20 and its variation in different leaves (both the upper and lower surface) situated at different level (0 level: leaf at the tip, 1 level: next leaf down to 0 level, 2 level: next leaf down to 1 level, 3 level: next leaf down to 2 level, 4 level: next leaf down to 3 level,) were characterized and finally all the trichome at different levels of the leaves were averaged, calculated per centimeter square leaf area. A peak trichome density was observed from 75 to 95 days in all the leaves at different levels except the leaf at the tip. At 0 level the leaves are at active developmental stage which may be cause for steady rate for trichome formation (Table 4).

TABLE 4

Trichome density(Trichomes/$cm^2$) in the leaves of the genotype CIMAP/MP20 at different developmental stages.

| Levels | 35 days stage | 55 days stage | 75 days stage | 95 days stage | 115 days stage |
|---|---|---|---|---|---|
| 0 | 1416 | 2816 | 5499 | 5392 | 5400 |
| 1 | 1223 | 2592 | 4373 | 5112 | 3106 |
| 2 | 982 | 1349 | 2443 | 2464 | 2392 |
| 3 | 875 | 1168 | 1813 | 2080 | 1668 |
| 4 | 610 | 752 | 1824 | 1205 | 1477 |

Taxonomic description of the peppermint plant CIMAP/MP20 are as given below:

1. Genus: *Mentha.*
2. Species: *piperita.*
3. Family: Lamiaceae.
4. Common name: Peppermint.
5. Plant height: 65–70 cm.
6. Plant canopy: 80–84 cm.
7. Growth habit: Herbaceous, erect and branched.
8. Stem: Quadrangular, woody, purplish green (59A).
9. Leaf: Simple, opposite, decussate.
   *Colour.*—Dark green (137A).
   *Texture.*—Chartaceous.
   *Surface.*—Glabrous dorsal surface, hairy on ventral veins.
   *Shape.*—Ovate-elliptical.
   *Margin.*—Serrate.
   *Tip.*—Acute-acuminate.
   *Base.*—Obtuse.
   *Size.*—Broad.
   *Petiole length.*—0.5 cm14 0.9 cm.
   *Area.*—7.91 $cm^2$.
   *Length.*—1.2 cm–4.3 cm.
   *Width.*—0.6 cm–2.6 cm.
10. Leaf: stem ratio: 1.06.
11. Inflorescence: Terminal spike.
12. Flowers: Arranged in whorls.
   *Pedicel.*—Smooth, green (137B).
   *Calyx.*—Glabrous, tubular, 5-lobed, margin ciliated, yellowgreen (146C).
   *Corolla.*—Purple, tubular, 4-lobed, lobes subequeal, white.
   *Anthers.*—Four, exserted, Grayed-red (181A).
   *Stigma.*—Bifid.

The colour codes are in accordance with The R.H.S. Colour Chart published by The Royal Horticultural Society, 80 Vincent Square, London SW1P 2PE,1995. The genotype CIMAP/MP20 was named and referred as 'Cim Indus' in this specification.

DNA Isolation and PCR Amplification Reactions

DNA was isolated from leaf tissue essentially according to the protocol described previously (Khanuja S P S, Shasany A K, Darokar M P & Sushil Kumar (1999) Rapid Isolation of PCR Amplifiable DNA from the Dry and Fresh Samples of Plants Producing Large Amounts of Secondary Metabolites and Essential oils by Modified CTAB Procedure. Plant Molecular Biology Reporter 17: 74.) and pooled DNA (equal amount from 20 individual plants of a genotype in a field) constituted the samples for polymerase chain reactions (PCRs) which were carried out in 25 μl volume.

A reaction tube contained 25 ng of DNA, 0.2 unit of Taq DNA polymerase, 100 μM each of dNTPs, 1.5 mM $MgCl_2$ and 5 p mol of decanucleotide primers. The amplifications were carried out using the DNA Engine thermal cycler (MJ Research, USA) following the protocol of Khanuja et al. (Khanuja S P S, Shasany A K, Srivastava A & Sushil Kumar (2000). Assessment of genetic relationships in *Mentha* species. Euphytica 111: 121–125.). The amplified products were loaded in 1.2% agarose gel containing 0.5 μg $ml^{-1}$ of ethidium bromide and photographed by Polaroid system. Twenty decamer primers procured from Operon Technologies, USA (OPA) were used to detect polymorphism in the selected genotype. The similarity matrix obtained after multivariant analysis using Nei and Li's coefficient (Nei, N. & W. Li, 1979.

Mathematical model for studying genetic variation in terms of restriction endonucleases. Proc. Natl. Acad. Sci. (USA) 76: 5269–5273.) is shown in Table 5. These similarity coefficients were used to generate a tree for cluster analysis using UPGMA method (FIG. 1) which shows the distinctiveness of the genotype CIMAP/MP20. The program 'NTSYS, Numerical Taxonomy System, Version 2.1, 2000' was employed to generate the cluster diagram from the similarity indices. The genotype CIMAP/MP20 was 54.1%, 50.2% and 51.1% different with the varieties 'Kukrail', 'Tushar' and 'Pranjal' respectively establishing the uniqueness of the genotype. These primers were also used to develop a unique RAPD profile of the chemotype 'Cim Indus' (FIG. 2). The band similarities were not derived from a photograph but were calculated directly from the RAPD profiles from the agarose gels based on which the cluster diagram was made.

TABLE 5

Similarity between the genotypes compared through RAPD profile analysis.

| | Kukrail | Tushar | Pranjal | CIMAP/MP20 |
|---|---|---|---|---|
| Kukrail | 1.000 | | | |
| Tushar | 0.960 | 1.000 | | |
| Pranjal | 0.950 | 0.960 | 1.000 | |
| CIMAP/MP20 | 0.459 | 0498 | 0.489 | 1.000 |

FIG. 2 illustrates the RAPD profile of the *Mentha piperita* genotype CIMPA/MP20. In this Figure Lane 1 represents the λ Hind III marker and lanes 2 to 21 represent, respectively, the profile for each of OPA 01 through OPA 20. The identities of the primers employed in OPA 01 through OPA 20 are provided in the accompanying sequence listing as SEQ ID NO:1 through SEQ ID NO:20, respectively.

Uniformity and Stability

Like any other *Mentha piperita* genotype this genotype is also planted vegetatively through runners and suckers. No variation of any kind was observed in this genotype for the last 3 years of trial maintaining the quality of oil and phenotype. The RAPD analysis of random plant samples in different years of trial also did not show any variation in profiles for this genotype indicating the stability of this genotype.

Disease and Pest Resistance

The incidence of lepidopteran pest *Spilarctia obliqua* and fungus mint rust (*Puccinia* sps), leaf spot and mildew were not detected in the field continuously for 3 years in the genotype CIMAP/MP20.

Metabolic Regulation of Menthofuran Biosynthesis

The genotype CIMAP/MP20 was rich in pulegone and menthofuran. In the biosynthetic pathway Geranyl pyrophosphate is converted to limonene which in turn is transformed into isopiperitenol, followed by pulegone. Pulegone is converted to menthone followed by menthol. Menthol and Menthone are the main constituents of the essential oil of *Mentha piperita.* In one branch of the pathway pulegone is converted to menthofuran. In this genotype the monoterpene pulegone is biosynthesized at an accelerated rate and the reaction favour more towards the menthofuran synthesis than menthol. In the initial stage (up to 55 days stage) of growth of this genotype the reaction favours for the production of menthol at a reduced rate from pulegone with less accumulation of pulegone and menthfuran. But at later stage as the plant matures the reaction favours accumulation of more menthofuran and pulegone and instead the biosynthesis of menthol decreases. This indicate the role of regulatory proteins in the monoterpene metabolism and the importance of this genotype for the isolation of such protein for future modification of metabolic pathway modification.

SEQUENCE LISTING

```
<160> NUMBER OF SEQ ID NOS: 20

<210> SEQ ID NO 1
<211> LENGTH: 10
<212> TYPE: DNA
<213> ORGANISM: Artificial
<220> FEATURE:
<223> OTHER INFORMATION: OPA primer

<400> SEQUENCE: 1

caggcccttc                                                          10


<210> SEQ ID NO 2
<211> LENGTH: 10
<212> TYPE: DNA
<213> ORGANISM: Artificial
<220> FEATURE:
<223> OTHER INFORMATION: OPA primer

<400> SEQUENCE: 2

tgccgagctg                                                          10


<210> SEQ ID NO 3
<211> LENGTH: 10
<212> TYPE: DNA
<213> ORGANISM: Artificial
<220> FEATURE:
<223> OTHER INFORMATION: OPA primer

<400> SEQUENCE: 3

agtcagccac                                                          10


<210> SEQ ID NO 4
```

-continued

<211> LENGTH: 10
<212> TYPE: DNA
<213> ORGANISM: Artificial
<220> FEATURE:
<223> OTHER INFORMATION: OPA primer

<400> SEQUENCE: 4 aatcgggctg 10

<210> SEQ ID NO 5
<211> LENGTH: 10
<212> TYPE: DNA
<213> ORGANISM: Artificial
<220> FEATURE:
<223> OTHER INFORMATION: OPA primer

<400> SEQUENCE: 5 aggggtcttg 10

<210> SEQ ID NO 6
<211> LENGTH: 10
<212> TYPE: DNA
<213> ORGANISM: Artificial
<220> FEATURE:
<223> OTHER INFORMATION: OPA primer

<400> SEQUENCE: 6 ggtccctgac 10

<210> SEQ ID NO 7
<211> LENGTH: 10
<212> TYPE: DNA
<213> ORGANISM: Artificial
<220> FEATURE:
<223> OTHER INFORMATION: OPA primer

<400> SEQUENCE: 7 gaaacgggtg 10

<210> SEQ ID NO 8
<211> LENGTH: 10
<212> TYPE: DNA
<213> ORGANISM: Artificial
<220> FEATURE:
<223> OTHER INFORMATION: OPA primer

<400> SEQUENCE: 8 gtgacgtagg 10

<210> SEQ ID NO 9
<211> LENGTH: 10
<212> TYPE: DNA
<213> ORGANISM: Artificial
<220> FEATURE:
<223> OTHER INFORMATION: OPA primer

<400> SEQUENCE: 9 gggtaacgcc 10

<210> SEQ ID NO 10
<211> LENGTH: 10
<212> TYPE: DNA
<213> ORGANISM: Artificial
<220> FEATURE:
<223> OTHER INFORMATION: OPA primer -continued

<400> SEQUENCE: 10 gtgatcgcag 10

<210> SEQ ID NO 11
<211> LENGTH: 10
<212> TYPE: DNA
<213> ORGANISM: Artificial
<220> FEATURE:
<223> OTHER INFORMATION: OPA primer

<400> SEQUENCE: 11 caatcgccgt 10

<210> SEQ ID NO 12
<211> LENGTH: 10
<212> TYPE: DNA
<213> ORGANISM: Artificial
<220> FEATURE:
<223> OTHER INFORMATION: OPA primer

<400> SEQUENCE: 12 tcggcgatag 10

<210> SEQ ID NO 13
<211> LENGTH: 10
<212> TYPE: DNA
<213> ORGANISM: Artificial
<220> FEATURE:
<223> OTHER INFORMATION: OPA primer

<400> SEQUENCE: 13 cagcacccac 10

<210> SEQ ID NO 14
<211> LENGTH: 10
<212> TYPE: DNA
<213> ORGANISM: Artificial
<220> FEATURE:
<223> OTHER INFORMATION: OPA primer

<400> SEQUENCE: 14 tctgtgctgg 10

<210> SEQ ID NO 15
<211> LENGTH: 10
<212> TYPE: DNA
<213> ORGANISM: Artificial
<220> FEATURE:
<223> OTHER INFORMATION: OPA primer

<400> SEQUENCE: 15 ttccgaaccc 10

<210> SEQ ID NO 16
<211> LENGTH: 10
<212> TYPE: DNA
<213> ORGANISM: Artificial
<220> FEATURE:
<223> OTHER INFORMATION: OPA primer

<400> SEQUENCE: 16 agccagcgaa 10

<210> SEQ ID NO 17

-continued

```
<211> LENGTH: 10
<212> TYPE: DNA
<213> ORGANISM: Artificial
<220> FEATURE:
<223> OTHER INFORMATION: OPA primer

<400> SEQUENCE: 17

gaccgcttgt                                                          10


<210> SEQ ID NO 18
<211> LENGTH: 10
<212> TYPE: DNA
<213> ORGANISM: Artificial
<220> FEATURE:
<223> OTHER INFORMATION: OPA primer

<400> SEQUENCE: 18

aggtgaccgt                                                          10


<210> SEQ ID NO 19
<211> LENGTH: 10
<212> TYPE: DNA
<213> ORGANISM: Artificial
<220> FEATURE:
<223> OTHER INFORMATION: OPA primer

<400> SEQUENCE: 19

caaacgtcgg                                                          10


<210> SEQ ID NO 20
<211> LENGTH: 10
<212> TYPE: DNA
<213> ORGANISM: Artificial
<220> FEATURE:
<223> OTHER INFORMATION: OPA primer

<400> SEQUENCE: 20

gttgcgatcc                                                          10
```

It is claimed:

1. A new and distinct mint plant of *Mentha piperita* variety 'Cim Indus', substantially as illustrated and described herein.

* * * * *

Figure 2:
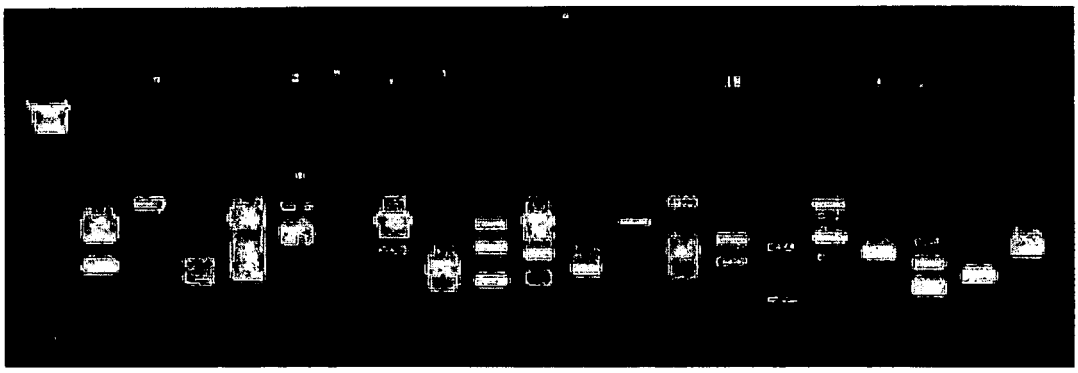
FIG. 2 shows the RAPD profile of the *Mentha piperita* genotype CIMPA/MP20.
Figure 3:
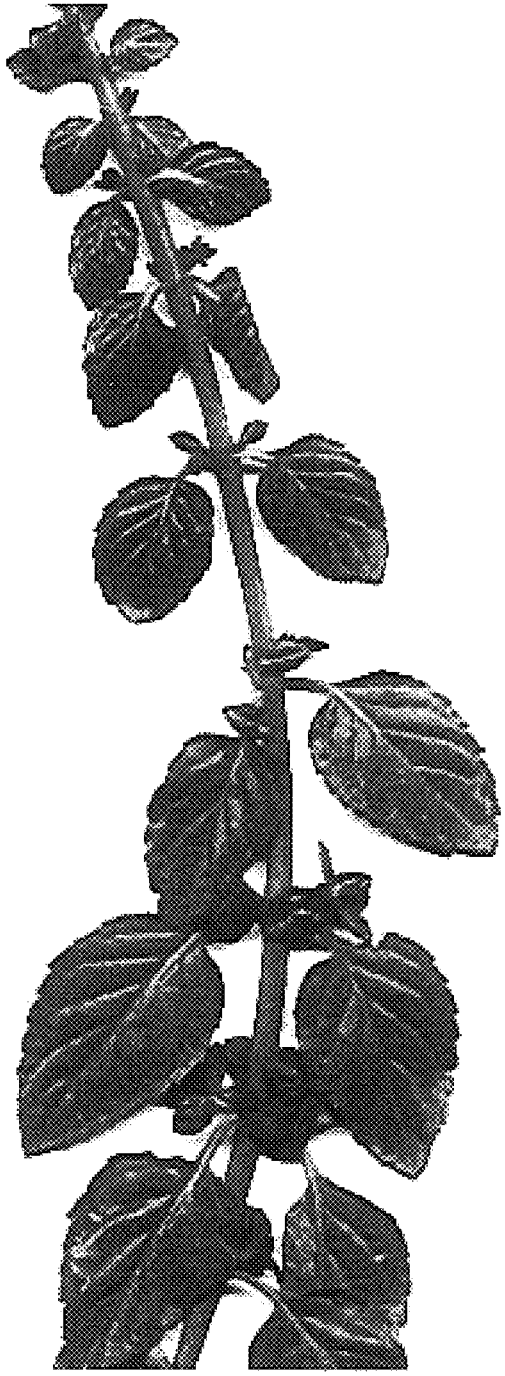
FIG. 3 shows a twig of CIMAP/MP20

FIG. 1: Cluster analysis for the chemotype 'Cim Indus' compared to 'Kukrail', 'Tushar' and 'Pranjal'.

FIG. 2: RAPD profile of the *Mentha piperita* genotype CIMAP/MP20

Lane 1: λ Hind III marker
Lane 2 to 21: Profile with OPA 01 to OPA 20.